United States Patent

Buttermann

[11] 3,939,204
[45] Feb. 17, 1976

[54] RADIOACTIVE FUNCTIONAL DIAGNOSTIC AGENTS

[75] Inventor: Götz Buttermann, Ottobrunn, Germany

[73] Assignee: Schering Aktiengesellschaft, Berlin & Bergkamen, Germany

[22] Filed: June 4, 1973

[21] Appl. No.: 366,461

[30] Foreign Application Priority Data
Dec. 22, 1972 Germany............................ 2264002
Jan. 10, 1973 Germany............................ 2300966

[52] U.S. Cl.. 260/518 A; 260/247.2 A; 260/293.79; 260/293.8; 260/294.8 B; 260/325 R; 260/326.41; 260/329 S; 260/345.7; 260/347.2; 260/404.5; 260/501.11; 260/516; 260/519; 424/5
[51] Int. Cl.² ...................................... C07C 103/30
[58] Field of Search .. 260/518 A, 519, 516, 501.11, 260/247.2 R, 404.5

[56] References Cited
UNITED STATES PATENTS

| | | | |
|---|---|---|---|
| 3,763,227 | 10/1973 | Ingelman | 260/519 |
| 3,770,820 | 11/1973 | Ackerman | 260/519 |
| 3,804,892 | 4/1974 | Ingelman | 260/519 |

Primary Examiner—Lorraine A. Weinberger
Assistant Examiner—L. A. Thaxton
Attorney, Agent, or Firm—Millen, Raptes & White

[57] ABSTRACT

This invention relates to triiodized dicarboxylic acid anilides containing radioactive iodine of the formula

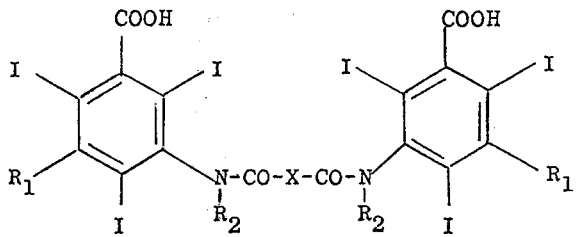

wherein
$R_1$ is hydrogen, carboxyl, N-acylamino, N-acylaminomethyl, N-alkyl-N-acylamino, N-butyrolactamyl, or an

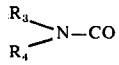

group, wherein $R_3$ and $R_4$ are each hydrogen, lower alkyl or hydroxyalkyl, or $R_3$ and $R_4$ together with the nitrogen atom form a 5 to 7 member heterocyclic ring which can contain a further oxygen, nitrogen or sulfur hetero atom;
$R_2$ is hydrogen, lower alkyl or hydroxyalkyl; and
X is straight-chain or branched alkylene of 1–14 carbon atoms, which can be interrupted by one or more oxygen or sulfur atoms,
as well as the physiologically acceptable salts thereof with suitable bases. These compounds are especially useful in the preparation of radioactive functional diagnostic agents.

21 Claims, No Drawings

RADIOACTIVE FUNCTIONAL DIAGNOSTIC AGENTS

CROSS-REFERENCE TO RELATED APPLICATION

Triiodized N-methyldicarboxylic acid anilides useful as radiopaque agents are described in copending, commonly assigned U.S. patent application Ser. No. 281,379, filed Aug. 17, 1972, the contents of which are incorporated by reference herein.

BACKGROUND OF THE INVENTION

This invention relates to triiodized carboxylic acid anilides and to processes for their preparation and use.

Compounds suitable for use as radiodiagnostic agents, especially for intravenous uro-, angio- and cholegraphy, must meet very high requirements with respect to vascular system compatibility and pharmacological inertness.

The use of radioactively labeled compounds as auxiliary agents for the observation and explanation of biochemical processes has been known for a long time: For example, for the development of medicines and for diagnostic purposes; i.e., for the liver function test, tetrachlorotetraiodofluorescein-$I^{131}$, bromthalein-$I^{131}$, and gold colloid $Au^{198}$ have been employed. However, these compounds all exhibit various disadvantages.

In the case of tetrachlorotetraiodofluorescein-$I^{131}$, it is difficult to produce a uniform unlabeled substance; moreover, during the labeling, radioactive by-products are formed having varying activity contents.

In the case of bromthalein-$I^{131}$, as with tetrachlorotetraiodofluorescein-$I^{131}$, the maximum accumulation in the liver and the elimination from the liver take place after a longer period of time, requiring longer examination times and a higher exposure to radiation.

Gold colloid $Au^{198}$ is only suitable for representing the liver by scintigraphy and does not provide a direct functional diagnosis.

In contrast thereto, it has now been found that dicarboxylic acid anilides, containing radioactive iodine, of this invention, as well as the salts thereof with physiologically compatible bases, do not exhibit these disadvantages. After being labeled with a radioactive iodine isotope, they represent excellent agents for the functional conductance of diagnostics on the hepatic cells themselves.

OBJECTS OF THE INVENTION

Accordingly, it is an object of this invention to provide novel radioactive triiodized dicarboxylic acid anilides.

Another object of this invention is to provide a process for preparing radioactive triiodized dicarboxylic acid anilides in good yields.

A further object of this invention is to provide useful radioactive diagnostic compositions and methods for their use.

Upon further study of the specification and appended claims, further objects and advantages of this invention will become apparent to those skilled in the art.

SUMMARY OF THE INVENTION

Briefly, the above and other objects of this invention are attained in one aspect by providing a compound of Formula I

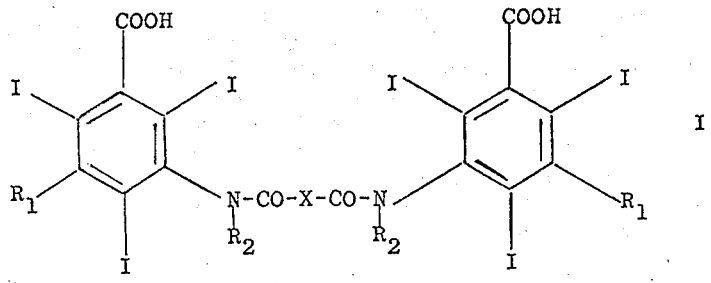

wherein
$R_1$ is hydrogen, carboxyl, N-acylamino, N-acylaminomethyl, N-alkyl-N-acylamino, N-butyrolactamyl, or an

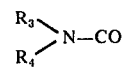

group, wherein $R_3$ and $R_4$ are each hydrogen, lower alkyl of hydroxyalkyl, or $R_3$ and $R_4$ together with the nitrogen atom form a 5 to 7 member heterocyclic ring which can contain a further oxygen, nitrogen or sulfur hetero atom;

$R_2$ is hydrogen, lower alkyl or hydroxyalkyl; and
X is straight-chain or branched alkylene of 1–14 carbon atoms, which can be interrupted by one or more oxygen or sulfur atoms,
as well as the physiologically acceptable salts thereof with suitable bases.

DETAILED DISCUSSION

The compounds of this invention according to Formula I include both the free compounds and their metal, ammonium and amine salts, preferably the water-soluble and non-toxic physiologically acceptable salts. These compounds, individually or in admixture, are valuable radioactive agents.

The term "dicarboxylic acid anilides containing radioactive iodine" as used herein refers to compounds wherein 1–6 inclusive iodine$^{127}$ atoms are replaced by a radioactive iodine isotope, e.g., iodine$^{131}$, iodine$^{123}$, iodine$^{125}$ or iodine$^{132}$.

The alkyl, alkoxy and acyl residues when present are preferably lower residues, e.g., lower alkyl of 1–6 carbon atoms, preferably 1–4 carbon atoms, such as methyl, ethyl, propyl, isopropyl or butyl; lower alkoxy of 1–4 carbon atoms, preperably 1–2 carbon atoms, such as methoxy or ethoxy; lower acyl, preferably lower alkanoyl of 1–6 carbon atoms, such as acetyl, propionyl, butyryl, isobutyryl, valeryl and hexanoyl. Preferred lower hydroxyalkyl groups are 2-hydroxyethyl or 3-hydroxypropyl.

Suitable salts of physiologically compatible bases include but are not limited to the alkali metal salts, e.g., sodium and lithium; the alkaline earth metal salts, e.g., calcium and magnesium; amine salts, e.g., ammonium, heterocyclic amines, e.g., morpholine and N-alkyl amines, hydroxyalkylamines, alkyl (hydroxyalkyl)-amines and di(hydroxyalkyl)-amines, wherein alkyl in each instance preferably contains 1–6, more preferably 1–4, carbon atoms, e.g., methyl, ethyl, n-propyl, 2-propyl, n-butyl, isobutyl, tert.-butyl, including trimethylamine, diethylamine, ethanolamine, diethanolamine and polyhydroxyalkylamines, e.g., trihydroxy-tert.-butylamine, saccharidyl amines, including glucamine, N-monoalkylglucamines and N,N-dialkylglucamines. Preferred mono- and dialkyl glucamines are those compounds which contain, in one or both alkyl groups respectively, a total of 1–4 carbon atoms; a hydroxy group can also be present when the alkyl group of these salts contains more than one carbon atom. Especially preferred alkylglucamine salts are the N-methyl and N,N-dimethyl salts.

Generally, compounds of Formula I are those in which $R_1$ is hydrogen, carboxyl, N-monoalkanoylamino, N-monoalkoxyalkanoylamino, N-alkyl-N-alkanoylamino, N-alkyl-N-alkoxyalkanoylamino, N,N-dialkanoylamino, N-alkanoylaminomethyl,

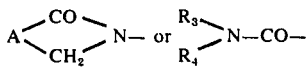

wherein A is alkylene of 2 or 3 carbon atoms and $R_3$ and $R_4$ are each hydrogen, lower alkyl or hydroxyalkyl, or $R_3$ and $R_4$ together with the nitrogen atom form a 5 to 7 member heterocyclic ring.

Preferred compounds of this invention are those of Formula I meeting one or more of the following definitions:

a. Compounds wherein $R_1$ is hydrogen, carboxyl, N-lower alkanoylamino, N-lower alkyl-N-lower alkanoylamino, N-butyrolactamyl; N-lower-alkanoylaminomethyl;
b. Compounds wherein $R_2$ is hydrogen, lower alkyl of 1–4 carbon atoms, 2-hydroxyethyl or 3-hydroxypropyl;
c. Compounds wherein $R_3$ and $R_4$ are each hydrogen, alkyl, of 1–4 carbon atoms, 2-hydroxyethyl or 3-hydroxypropyl;
d. Compounds wherein $R_3$ and $R_4$ together with the nitrogen atom form a 5 to 7 member heterocyclic ring containing 0–1 further oxygen atoms, e.g., a morpholine, piperidine or pyrrolidine ring;
e. Compounds wherein X is alkylene of 2–6 carbon atoms interrupted by a single oxygen or sulfur atom, the sulfur atom when present being preferably but not necessarily present in the reduced bivalent state;
f. Compounds wherein X is alkylene of 2–14 carbon atoms interrupted at every second or third carbon atom by an oxygen or sulfur atom;
g. Compounds wherein X is alkylene of 1–14 carbon atoms.

Specific compounds of Formula I, in addition to those shown in the Examples, include 4,7,10,13-tetraoxahexadecane1,16-dioyl bis(3-carboxy-2,4,6-triiodo-N-methylanilide)
nonane-1,9-dioyl bis(3-carboxy-5-acetamidomethyl-2,4,6-triiodoanilide)
diglycolic acid bis(3-carboxy-5-acetamidomethyl-2,4,6-triiodoanilide)
diglycolic acid bis(3-carboxy-5-acetamidomethyl-2,4,6-triiodoanilide)
thiodiglycolic acid bis(3-carboxy-2,4,6-triiodo-N-methylanilide).

Preferred dicarboxylic acid anilides are:
diglycolic acid bis(3-carboxy-2,4,6-triiodoanilide)
adipic acid bis(3-carboxy-2,4,6-triiodoanilide)
3,6,9-trioxaundecane-1,11-dioyl bis(3-carboxy-2,4,6-triiodoanilide)
4,7,10,13-tetraoxahexadecane-1,16-dioyl bis(3-carboxy-2,4,6-triiodoanilide)
4,7,10-trioxatridecane-1,13-dioyl bis(3-carboxy-2,4,6-triiodoanilide)
nonane-1,9-dioyl bis(3-carboxy-5-acetamidomethyl-2,4,6-triiodoanilide)
diglycolic acid bis(3-carboxy-2,4,6-triiodo-N-methylanilide)
3,6,9-trioxaundecane-1,11-dioyl bis(3-carboxy-2,4,6-triiodo-N-methylanilide).

Equivalents of the compounds of this invention bearing a lower-alkanoyl group are compounds otherwise corresponding structurally thereto and possessing the same activity where instead of a lower-alkanoyl group there is present the acyl group of another organic acid, e.g., a carboxylic-acid containing up to 15 carbon atoms, especially aliphatic carboxylic, preferably an alkanoic acid, which can be unsaturated, branched, polybasic, or substituted in the usual manner, e.g., by hydroxy or halogen atoms; a cycloaliphatic, aromatic or mixed aromatic-aliphatic (alkaryl or aralkyl) acid, which can likewise be substituted in the usual manner, examples of preferred acids being formic acid, acetic acid, hydroxyacetic acid, propionic acid, butyric, isobutyric, α-ethylbutyric, valeric, isovaleric, α-ethylvaleric, 2-methylbutyric, 3-ethylbutyric, hexanoic, diethylacetic, triethylacetic, octanoic and palmitic acid; caproic acid, enanthic acid, undecyclic acid, oleic acid, trimethylacetic acid, dichloroacetic acid, cyclopentylpropionic acid, phenylpropionic acid, phenylacetic acid, phenoxyacetic acid, succinic acid and benzoic acid; a cyclic acid, preferably a cycloaliphatic acid containing 5–18 carbon atoms, e.g., cyclopropylideneacetic, cyclobutylcarboxylic, cyclopentylcarboxylic, cyclopentylacetic, cyclohexyl carboxylic, cyclohexylacetic and β-cyclohexylpropionic acid; a carbocyclic aryl or alkaryl acid containing 6–18 carbon atoms and 1 or 2 rings, e.g., benzoic, 2-, 3- or 4-methylbenzoic, 2,3-, 2,4-, 2,5-, 2,6-, 3,4- and 3,5-dimethylbenzoic, ethylbenzoic, 2,3,6-trimethylbenzoic and 3-methyl-α-naphthoic acid; an aralkyl acid containing 7 to 18 carbon atoms, e.g., β-phenylpropionic; a polybasic acid containing 2–18 carbon atoms and 1 to 5 hydroxy groups, e.g, glycolic, lactic, citric, tataric, d-maleic, d-glyceric and salicyclic acid; the corresponding acids containing one, two or more of simple substituents, e.g., halo, alkoxy, acyloxy, etc., in the molecule, e.g., chloroacetic, fluoroacetic, trichloroacetic, trifluoroacetic, 2,3,4-trimethoxybenzoic, phenoxyacetic, α-naphthoxyacetic acid, etc.

The acyl group of such equivalent compounds can also be that of a sulfonic acid, e.g., an arylsulfonic, including benzenesulfonic, p-toluene-sulfonic, m,m'-dimethylbenzenesulfonic, o,o'-dimethylbenzenesulfonic, sym.-trimethylbenzenesulfonic, sym.-triethylbenzenesulfonic, m-ethylbenzenesulfonic, para-isopropylbenzenesulfonic, m-n-butylbenzenesulfonic acid, or an alkylsulfonic, e.g., methanesulfonic, ethanesulfonic, propanesulfonic, isopropanesulfonic, butanesulfonic, tert.-butanesulfonic, pentanesulfonic, isopentanesulfonic, hexanesulfonic, heptanesulfonic, octylsulfonic or heterocyclic sulfonic, e.g., α-pyridinesulfonic, α-pyranesulfonic, α-thiophensulfonic, α-furansulfonic, α-tetrahydrofuransulfonic, or other alkyl-, carboxyclic and heterocyclic aryl-, alkaryl-and aralkyl-sulfonic acid, preferably one containing 1–8 carbon atoms and 0–2, preferably 0–1 N, S or O heteroatoms, which are preferably ring carbon atoms in a heterocyclic ring.

The radioactive compounds of Formula I can be prepared either by radioactively labeling corresponding nonradioactive compounds or by synthesis from radioactive starting materials. While the radioactive iodines are greatly preferred for diagnostic agents, it will be apparent that other radioactive atoms can likewise be used depending on the type of radiation and radioactive half life suitable for a given purpose e.g., bromine-82, etc.

Compounds of Formula I can be prepared by reacting a compound of Formula II

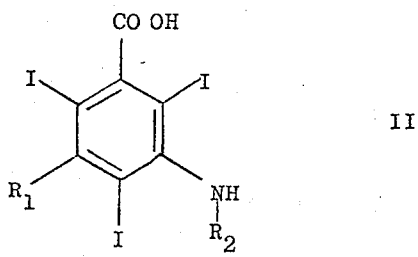

wherein $R_1$ and $R_2$ have the above-indicated values, with a dicarboxylic acid dihalide derivative of Formula III

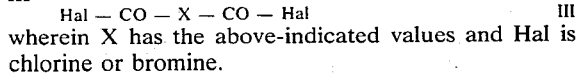

wherein X has the above-indicated values and Hal is chlorine or bromine.

The reaction of an acid of Formula II with a dicarboxylic acid derivative of Formula II is preferably effected in an inert solvent at elevated temperatures, e.g., at temperatures of 60°–140° C. Suitable inert solvents include but are not limited to dioxane, toluene, dimethylformamide and dimethylacetamide.

For the formation of the physiologically acceptable salt, the conventional pharmaceutical bases can be employed, especially sodium hydroxide, glucamine, N-methylglucamine, N,N-dimethylglucamine, ethanolamine, diethanolamine, morpholine, etc.

The radioactive compounds of this invention are conveniently produced by heating one or more compounds of Formula I to be radioactively labeled in an aqueous solution or in a melt of one or more low-melting compounds with a maximally carrier-free alkali or alkaline earth radioiodide. Suitable low-melting compounds include but are not limited to N,N-dimethyl-p-toluenesulfonamide, N,N'-bis(dimethylamino)-sulfone, dimethylsulfone, or mixtures thereof. Suitable alkali or alkaline earth radioiodides include but are not limited to sodium, calcium etc.

The reaction is generally effected in the case of aqueous solutions at boiling temperature for a period of time sufficient to effect labelling, generally of 15 minutes to 12 hours, and using a molar ratio of radioiodide to the compound of Formula I which varies according to the desired degree of labelling. As far as a melt is used, the reaction is generally effected at a temperature of 50° to 300°C. for a period of time sufficient to effect labelling, generally of 15 minutes to 12 hours.

The compounds of this invention can be employed in mixture with conventional excipients, i.e., pharmaceutically acceptable organic or inorganic carrier substances suitable for intravenous administration, the soluble salts of this invention are preferably used in aqueous solution whereby the concentration of the salts is preferably about 0.1–50% by weight and wherein the radioactivity per ml. is 0.025–25 mc, preferably 1–10 mc.

The acids, in the form of their water-soluble, physiologically compatible salts, are extraordinarily good radioactive diagnostic agents for evaluating liver functions. The salt solutions are characterized by a extremly low viscosity and accordingly can be administered by intravenous injection. The salt solutions are furthermore distinguished by a good circulatory compatibility and a low toxicity.

For a functional test, depending on the half-life period of the particular iodine isotope employed, it is generally desirable to intravenously inject into humans solutions containing a total radioactivity of 0.1–5 mc., preferably 0.1–1.5 mc.

Consequently, the present invention also relates to a radioactive functional diagnostic agent, comprising an iodine-labeled dicarboxylic acid anilide of the general Formula I in the form of the water-soluble salts thereof with physiologically compatible bases, characterized in that it is present in the form of aqueous solutions containing per 10 ml. of water, 1 mg. to 5 g. of iodine-labeled dicarboxylic acid anilide, wherein the radioactivity per 1 ml. ranges between 0.025 mc. and 25 mc.

Compounds of Formula I are particularly useful in the preparation of a radioactive functional diagnostic agent comprising an iodine-labeled dicarboxylic acid anilide of Formula I, preferably in the form of the water-soluble salts thereof with physiologically compatible bases. Generally, 1 mg. to 5 g., preferably 10–100 mg., of iodine-labeled dicarboxylic acid anilide and an equivalent amount of one or more physiologically compatible bases are dissolved, per 10 ml. of water, the solution is filled into ampoules or multivials and sterilized to provide a diagnostic agent wherein the radioactivity per 1 ml. ranges between 0.025 mc. and 25 mc., preferably 1–10 mc.

It will be appreciated that the radioactive compounds of this invention are normally present in combination with a major amount of the corresponding unlabeled compounds, since the labelling process is largely random and only a small percentage of the molecules need be labeled.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, the temperatures are set forth in degrees Celsius. Unless otherwise indicated, all parts and percentages are by weight.

EXAMPLE 1

The following table lists the characteristic properties of the compound A of this invention and those of the conventional compounds B and C.

A: Diglycolic acid bis(3-carboxy-2,4,6-triiodoanilide)-131-iodine N-methylglucamine salt.

B: Tetrachlorotetraiodofluorescein-131-iodine sodium salt.

C: Bromthalein-131-iodine sodium salt.

These compounds were tested intravenously on humans. The total quantity of radioactivity per injection of the respectively injected aqueous test solution was approximately 0.25 millicurie in each instance.

The distribution in the body as function of time after administration was measured by scinticamera in the usual manner.

TABLE

| Compound | Maximum Liver Accumulation (min.) | Time of Appearance in Intestine (min.) | Time of Appearance in Gallbladder (min.) | Blood T ½ (min.) | Liver T ½ (min.) |
|---|---|---|---|---|---|
| A | 16.5 | 14.6 | 25.5 | 3.22 | 3.19 |
| B | 30 | 45 | 45 | 8.14 | 10.24 |
| C | 30 | 15 | 45 | 4.5 | |

The table clearly shows the superiority of compound A of this invention as compared to the conventional compounds B and C. The maximum accumulation of compound A in the liver occurs after only 16.5 minutes, and times of appearance in the intestine and gallbladder are also markedly shorter than in the comparison substances B and C. The rapid elimination from the blood into the liver cells and from the liver cells into the bile ducts and gallbladder is demonstrated by the brief half-life periods T ½.

The values T ½ indicate a markedly faster liver passage for compound A, resulting in a better differentiated uptake curve and images of greater contrast. Because of this, the duration of the examination is shortened by one-third. Moreover, the rapid course of the liver passage function, together with the faster elimination, further reduces a patient's exposure to the radiation. Additionally, in the case of patients having a healthy liver, a concomitant gallbladder representation is obtained, in contrast to substances B and C; and it is thus possible to simultaneously obtain a gallbladder kinetics representation in a single diagnostic test. The absence of an enterohepatic cycle in compound A, i.e., the lack of reabsorption of the radioactive functional diagnostic agent passed into the intestine with the bile and into the bloodstream, is of special advantage, as this feature results in a reduction of the radiation load exposure and simultaneously substantially facilitates the calculation of the data set forth in the table.

Accordingly, compounds of Formula I are highly suitable as agents for evaluating the liver function, as well as for the representation and functional diagnosis of the bile ducts and the gallbladder.

EXAMPLE 2

100 mg. of diglycolic acid bis(3-carboxy-2,4,6-triiodoanilide) methylglucamine salt is dissolved in 10 ml. of water at a pH of about 6.5, mixed with 1 ml. of sodium acetate buffer, and the desired activity quantity is added as an aqueous sodium iodide$^{131}$ solution — maximally carrier-free, e.g., 10 mc. The solution is heated under reflux for 15 minutes. After cooling, the solution is acidified with 2N hydrochloric acid, and the thus-precipitated product is vacuum-filtered. The precipitated 131iodine-labeled diglycolic acid bis(3-carboxy-2,4,6-triiodoanilide) is again suspended in 10 ml. of water, dissolved with sodium hydroxide solution, and reprecipitated with hydrochloric acid. The product, in a more than 90% yield, chemically as well as radiochemically, is diglycolic acid bis(3-carboxy-2,4,6-triiodoanilide)-131-iodine. In place of the iodine isotope $I^{131}$, it is also possible to employ any other radioactive iodine isotope, such as $I^{123}$, $I^{125}$ and $I^{132}$.

Analogously to Example 1, the following compounds can be labeled with 131-, 123-, 125- and 132 iodine:

adipic acid bis(3-carboxy-2,4,6-triiodoanilide), 4,7,10,13-tetraoxahexadecane-1,16-dioyl bis(3-carboxy-2,4,6-triiodoanilide), 4,7,10-trioxatridecane-1,13-dioyl bis(3-carboxy-2,4,6-triiodoanilide), nonane-1,9-dioyl bis(3-carboxy-5-acetamidomethyl-2,4,6-triiodoanilide), 3,6,9-trioxaundecane-1,11-dioyl bis(3-carboxy-2,4,6-triiodoanilide).

EXAMPLE 3

An aqueous solution of sodium iodide 131, maximally carrier-free, containing 10 mc. is dried in a small flask under a nitrogen atmosphere. Thereafter, 100 mg. of N,N-dimethyl-p-toluenesulfonamide is added thereto and the mixture is heated to 120°C., until it melts. 25 mg. of diglycolic acid bis(3-carboxy-2,4,6-triiodoanilide) is added to the melt, and a clear melt is thus formed. After 1 hour, the melt is allowed to cool, the solidified mass is dissolved in 3 ml. of acetone, and stirred into ice-cooled aqueous ammonia solution. After the insoluble matter has been filtered off, the solution is acidified. The thus-precipitated diglycolic acid bis(3-carboxy-2,4,6-triiodoanilide)-131-iodine is vacuum-filtered and once reprecipitated as described in Example 2. In a chemical and radiochemical yield of more than 90%, one obtains diglycolic acid bis(3-carboxy-2,4,6-triiodoanilide)-131-iodine. Analogously to Example 3, diglycolic acid bis(3-carboxy-2,4,6-triiodo-N-methylanilide) and 3,6,9-trioxaundecane-1,11-dioyl bis(3-carboxy-2,4,6-triiodo-N-methylanilide) can be labeled with 131-, 123-, 125- and 132-iodine.

EXAMPLE 4

Production of a ready-for-use solution for intravenous injection of diglycolic acid bis(3-carboxy-2,4,6-triiodoanilide)methylglucamine salt-131-iodine:

| | | |
|---|---|---|
| 131-iodine, radioactivity 10 mc. | 0.100 | g. |
| N-methylglucamine | 0.034 | g. |
| disodium edetate | 0.1 | mg. |
| twice distilled water ad | 10 | ml. |

This solution is filled into a multivial and sterilized at 120° C. The solution thus contains, at the time of preparation, 1 mc./ml.

For a functional test, there is withdrawn from this solution, for example, 0.25 ml. — containing 0.25 mc. $I^{131}$ as [diglycolic acid bis(3-carboxy-2,4,6-triiodoanilide) methylglucamine salt]-131-iodine, and injected intravenously.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:
1. A radioactive compound selected from the group consisting of dicarboxylic acid anilides of the formula

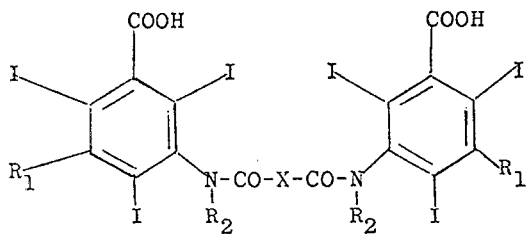

wherein
1–6 of said iodine atoms are in the form of a radioactive iodine isotope;
$R_1$ is hydrogen, carboxyl, N-alkanoyl, N-alkanoylaminomethyl, N-alkyl-N-alkanoylamino or

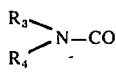

wherein $R_3$ and $R_4$ are each hydrogen, lower alkyl or hydroxyalkyl;
$R_2$ is hydrogen, lower alkyl or hydroxyalkyl;
X is alkylene of 1–14 carbon atoms which can be interrupted by one or more oxygen or sulfur atoms; and
the physiologically acceptable salts thereof.

2. A compound according to claim 1 wherein $R_1$ is hydrogen, carboxyl, N-lower alkanoylamino, N-lower alkyl-N-lower alkanoylamino or N-lower-alkanoylaminomethyl.

3. A compound according to claim 1 wherein $R_2$ is hydrogen, alkyl of 1–4 carbon atoms, 2-hydroxyethyl or 3-hydroxypropyl.

4. A compound according to claim 1 wherein $R_3$ and $R_4$ are each hydrogen, alkyl of 1–4 carbon atoms, 2-hydroxyethyl or 3-hydroxypropyl.

5. A compound according to claim 1 wherein X is alkylene of 2–6 carbon atoms interrupted by a single oxygen or sulfur atom.

6. A compound according to claim 1 wherein X is alkylene of 2–14 carbon atoms interrupted at every second or third carbon atom by an oxygen or sulfur atom.

7. A compound according to claim 1 selected from the group consisting of diglycolic acid bis(3-carboxy-2,4,6-triiodoanilide)-131-, -123-, -125- and -132-iodine and the physiologically acceptable salts thereof.

8. A compound according to claim 1 selected from the group consisting of adipic acid bis(3-carboxy-2,4,6-triiodoanilide)-131-, -123-, -125- and -132-iodine and the physiologically acceptable salts thereof.

9. A compound according to claim 1 selected from the group consisting of 4,7,10,13-tetraoxahexadecane-1,16-dioyl bis(3-carboxy-2,4,6-triiodoanilide)-131-, -123-, -125- and -132-iodine and the physiologically acceptable salts thereof.

10. A compound according to claim 1 selected from the group consisting of 4,7,10-trioxatridecane-1,13-dioyl bis(3-carboxy-5-acetamidomethyl-2,4,6-triiodoanilide)-131-, -123-, -125- and -132- iodine and the physiologically acceptable salts thereof.

11. A compound according to claim 1 selected from the group consisting of nonane-1,9-dioyl bis(3-carboxy-5-acetamidomethyl-2,4,6-triiodoanilide)-131-, -123-, -125-and -132-iodine and the physiologically acceptable salts thereof.

12. A compound according to claim 1 selected from the group consisting of 3,6,9-trioxaundecane-1,11-dioyl bis(3-carboxy-2,4,6-triiodo-N-methylanilide)-131-, -123-, -125- and -132-iodine and the physiologically acceptable salts thereof.

13. A compound according to claim 1 selected from the group consisting of diglycolic acid bis(3-carboxy-2,4,6-triiodo-N-methylanilide)-131-, -123-, -125- and -132-iodine and the physiologically acceptable salts thereof.

14. A compound according to claim 1 selected from the group consisting of 3,6,9-trioxaundecane-1,11-dioyl bis(3-carboxy-2,4,6-triiodoanilide)-131-, -123-, -125- and -132-iodine and the physiologically acceptable salts thereof.

15. A compound according to claim 1 wherein X is alkylene of 1–14 carbon atoms.

16. A compound according to claim 1 wherein $R_1$ is hydrogen or carboxyl.

17. A compound according to claim 16, wherein $R_1$ is hydrogen.

18. A compound according to claim 17, wherein $R_2$ is hydrogen, lower alkyl of 1–4 carbon atoms, 2-hydroxyethyl or 3-hydroxypropyl.

19. A compound according to claim 17, wherein X is alkylene of 1–14 carbon atoms.

20. A compound according to claim 18, wherein X is alkylene of 1–4 carbon atoms.

21. A process for the preparation of radioactive dicarboxylic acid anilides containing radioactive iodine, according to claim 1, which comprises heating the dicarboxylic acid anilide to be labeled in an aqueous solution or in a melt of one or more low-melting substances, with a carrier-free alkali or alkaline earth radioiodide to form said anilide.

* * * * *